US010101198B2

(12) United States Patent
    Zorbach

(10) Patent No.: US 10,101,198 B2
(45) Date of Patent: *Oct. 16, 2018

(54) APPARATUS FOR AN OPTICAL IN-SITU GAS ANALYSIS

(71) Applicant: SICK AG, Waldkirch (DE)

(72) Inventor: Ralf Zorbach, Waldkirch (DE)

(73) Assignee: SICK AG, Waldkirch (DE)

( * ) Notice: Subject to any disclaimer, the term of this patent is extended or adjusted under 35 U.S.C. 154(b) by 23 days.

This patent is subject to a terminal disclaimer.

(21) Appl. No.: 15/410,892

(22) Filed: Jan. 20, 2017

(65) Prior Publication Data

US 2017/0219425 A1    Aug. 3, 2017

(30) Foreign Application Priority Data

Feb. 1, 2016   (DE) .......................... 10 2016 101 720

(51) Int. Cl.
| | |
|---|---|
| *G01N 21/00* | (2006.01) |
| *G01J 1/02* | (2006.01) |
| *G01J 1/04* | (2006.01) |
| *G01N 21/27* | (2006.01) |
| *G01N 21/3504* | (2014.01) |
| *G01N 21/15* | (2006.01) |
| *G01N 21/85* | (2006.01) |

(52) U.S. Cl.
CPC .......... *G01J 1/0295* (2013.01); *G01J 1/0403* (2013.01); *G01N 21/276* (2013.01); *G01N 21/15* (2013.01); *G01N 21/3504* (2013.01); *G01N 21/85* (2013.01); *G01N 2021/8585* (2013.01)

(58) Field of Classification Search
CPC .......... G01J 1/00; G01J 1/0295; G01J 1/0403; G01N 21/01; G01N 21/59; G01N 21/276; G01N 21/15; G01N 21/3504; G01N 21/85; G01N 2021/8585
See application file for complete search history.

(56) References Cited

U.S. PATENT DOCUMENTS 4,549,080 A * 10/1985 Baskins ............. G01N 21/3504
                                                  250/338.1

FOREIGN PATENT DOCUMENTS

DE        102014002087 A1 *   8/2015   ......... G01N 21/3504

OTHER PUBLICATIONS

Office Action dated Sep. 14, 2016 for DE corresponding application.

* cited by examiner

*Primary Examiner* — Jamil Ahmed
(74) *Attorney, Agent, or Firm* — Nath, Goldberg & Meyer; Jerald L. Meyer

(57) ABSTRACT

An apparatus for an optical in-situ gas analysis includes a housing; a measuring lance whose one first end is connected to the housing and whose other second end projects into the gas to be measured; a light transmitter that is arranged in the housing and whose light is conducted into the measuring lance and is reflected by a reflector arranged at the second end onto a light receiver, and the optical path defines an optical measurement path within the measuring lance; a gas-permeable filter that is held in the measuring lance and in whose interior the measurement path is located: and an evaluation device for evaluating received light signals of the light receiver. It is proposed to be able to reduce the consumption of test gas that the measuring lance has coaxially arranged inner and outer pipes and the outer pipe has openings for the gas to be measured.

5 Claims, 3 Drawing Sheets

APPARATUS FOR AN OPTICAL IN-SITU GAS ANALYSIS

Figure 1:
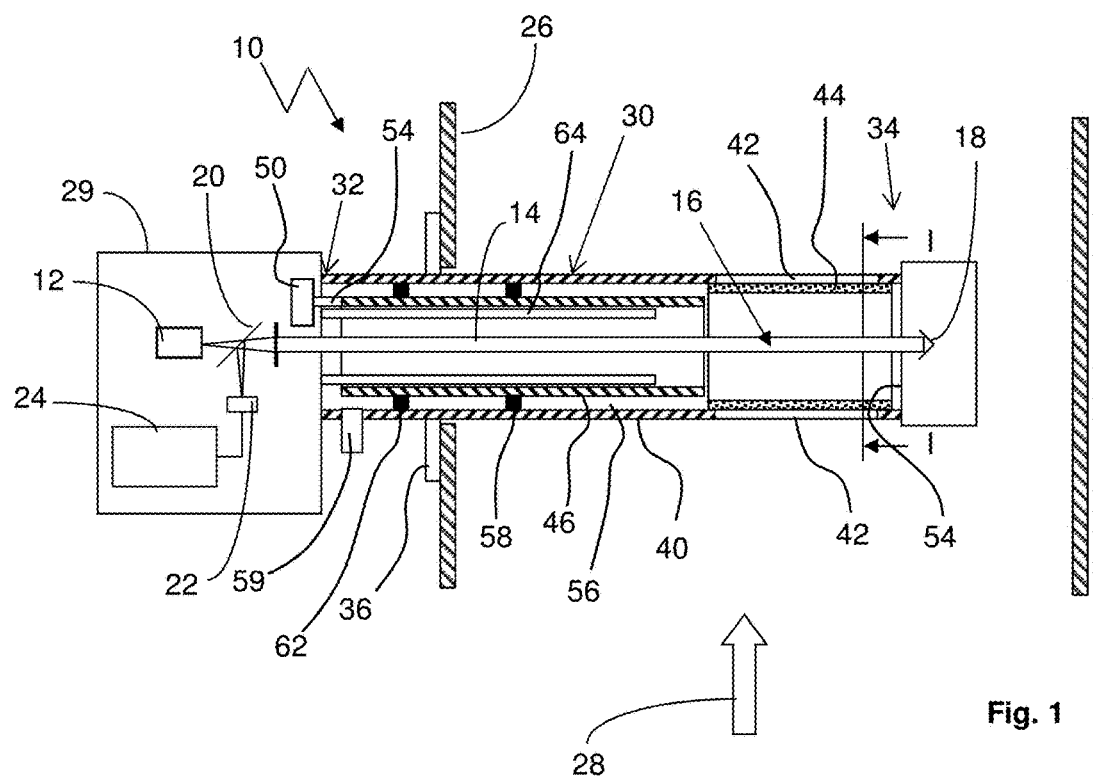

The invention relates to an apparatus for an optical in-situ gas analysis in accordance with the preamble of claim 1.

Specific gas portions, e.g. hydrogen sulfide, carbon monoxide, SO2, NH3, NO NO2, HCl, FH or the like, are measured by means of optical transmission or light scattering using such apparatus. The concentration of these gas portions is mostly determined in this respect.

Fields of application are, for example, emission measurements of industrial plant in which the flue gases in the flue gas passage have to be monitored with respect to their content of specific molecular compounds. The gas flows to which the optoelectronic apparatus is exposed to measure the desired gas portions are frequently characterized by high particulate loads such as smoke, dusts or other aerosols. These high particulate loads cause a high light absorption and/or a high light scattering that greatly impedes the actual measurement, up to making it impossible. Hydrogen sulfide, for example, thus has a very wide absorption as well as ultrafine dust. It is then no longer possible to distinguish whether the absorption emanates from hydrogen sulfide or from the dust.

It is known to provide filters to keep out such particulates that interfere with the measurement (e.g. U.S. Pat. No. 4,549,080), said filters comprising a pipe of porous material in whose interior the measurement path is located. The gas to be measured can admittedly enter into the measurement path due to the porous structure, but particulates such as smoke, dusts or aerosols can be kept way in dependence on the pore size.

It is disadvantageous that such in-situ devices have to be tested, checked or calibrated from time to time and a test gas has to be introduced into the measurement path for this purpose. The test gas is blown into the measurement path for this purpose. The measurement path is, however, not hermetically sealed, but the test gas rather escapes through the pores of the filter into the flue gas passage. A sufficient quantity of test gas therefore has to be permanently blown into the measurement path at sufficient pressure for the duration of the calibration measurements. The test gas quantity required for a calibration is correspondingly high. This disadvantage in particular becomes noticeable with long measurement paths having a correspondingly long, porous filter.

Starting from this prior art, it is the object of the invention to provide an improved apparatus with which the consumption of test gas can be reduced.

This object is satisfied by an apparatus having the features of claim 1.

The apparatus in accordance with the invention for an optical in-situ gas analysis comprises
  a housing;
  a measuring lance whose one first end is connected to the housing and whose other second end projects into the gas to be measured;
  a light transmitter that is arranged in the housing and whose light is conducted into the measuring lance and is reflected by a reflector arranged at the second end onto a light receiver and the optical path defines an optical measurement path within the measuring lance;
  a gas-permeable filter that is held in the measuring lance and in whose interior the measurement path is located:
  and an evaluation device for evaluating received light signals of the light receiver.

In accordance with the invention, the measuring lance has an inner pipe and an outer pipe that are arranged coaxially with respect to one another. The outer pipe has openings for the gas to be measured. The inner pipe and the outer pipe are displaceable with respect to one another in the longitudinal pipe direction to close the openings in a test mode of operation. An annular gap between the inner pipe and the outer pipe is sealed by a seal that is formed by at least one piston ring.

The openings toward the measurement path are closed by the inner pipe so that measurement gas can no longer enter into the measurement path. The measurement path can then be flooded with test gas. A defined leak, that may be small, however, is sensible in this respect to displace measurement gas still present after closing the openings out of the measurement path by the test gas. The test gas can, however, only escape through the small defined leaks and no longer through the filter. A test gas filling of the measurement path is achieved by a small excess pressure in the arising measurement chamber in connection with a constant test gas flow. The test gas consumption thus becomes able to be calculated and can be substantially minimized and is also very largely independent of the length of the active measurement path. The measurement path is furthermore uniformly filled with test gas. The test gas consumption is constant and predictable.

The embodiment in accordance with the invention having the piston rings is a comparatively simple design of the outer pipe and inner pipe, which brings along a cost saving since standard pipes and standard piston rings can be used for the outer pipe and for the inner pipe. Piston rings are resilient and can adapt to the inner pipe diameter, whereby temperature fluctuations are also unproblematic.

Piston rings are standard wear parts and are correspondingly available in an inexpensive manner, are commercial and can be procured regionally, independently of the country, which contributes to a high service and repair friendliness. Standard wear parts such as piston rings can also be simply replaced in-house.

The inner pipe and outer pipe are sealed in a defined manner with respect to one another by the piston rings and simultaneously effect a centering of the inner pipe.

A further advantage of the piston rings is a safe operation even under harsh conditions such as salt formation in the measuring lance during start-up and shutdown procedures of the plant. The degree and kind of pollution are inter alia dependent on the composition of the measurement gas, on the plant operation mode and on the temperature fluctuations in the measurement gas. For example, salts that move through the filter in the gas phase can crystallize at the inner surfaces of the lance on a drop in measurement gas temperature since the temperature drop at the inner lance surface can be faster than the gas diffusion through the filter. Such contaminants/deposits are simply "scraped off" by the edges of the piston rings on the moving in and out of the inner pipe. The piston rings namely run along the inner wall of the outer pipe. This opens up the possibility of regularly eliminating such deposits by a periodic moving in and out of the inner pipe.

The test mode of operation could be carried out automatically at defined time intervals or by manual actuation. This would be reflected in price-graduated variants of the apparatus in accordance with the invention.

In an embodiment of the invention, the piston ring comprises bronze or brass and the outer pipe comprises steel. This suitable material combination reduces the friction between the piston ring and thus between the inner pipe and the outer pipe. The friction can be further reduced by minimizing the sliding surfaces of the piston ring, e.g. by a suitable shape, to increase the smooth running.

The inner pipe could also be designed of Teflon. Since the coefficient of expansion of Teflon is smaller than that of steel, the Teflon pipe can also not jam on heating.

Two piston rings spaced apart in the longitudinal pipe direction are provided for a better guidance and for an avoidance of jamming.

In a further development of the invention, the inner pipe is guided by guide elements and is displaceable by an electric motor. Associated electromechanical drive components can be arranged distributed at the first end of the lance. The movement of the inner pipe is preferably guided by two or three bars arranged distributed equidistantly over the periphery. The pulling/thrust force is evenly distributed over the periphery of the inner pipe by the spatial distribution of the guide elements.

In an embodiment of the invention, a drive can be configured to move the inner pipe by magnets when e.g. the inner pipe has fixedly arranged magnets that interact with electrically controllable magnets arranged at the guide elements.

A Bowden cable or a drive over a threaded spiral in combination with stepper motors would alternatively also be conceivable as the drive. Linear motors could also be used as a further alternative.

A test gas connector is sensibly provided at the measuring lance or at the housing to be able to fill the measurement path with a test gas via it.

A heating spiral outwardly contacting the outer pipe can prevent the entry of water on applications in a wet measurement gas.

Figure 2:
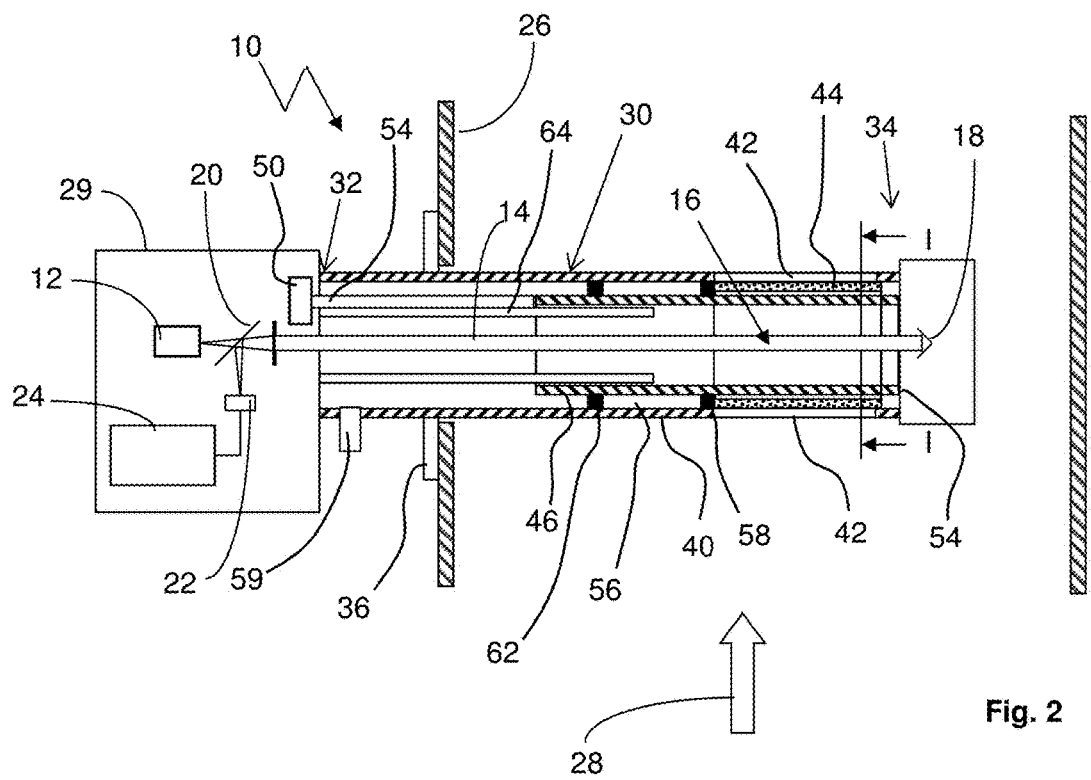
Figure 3:
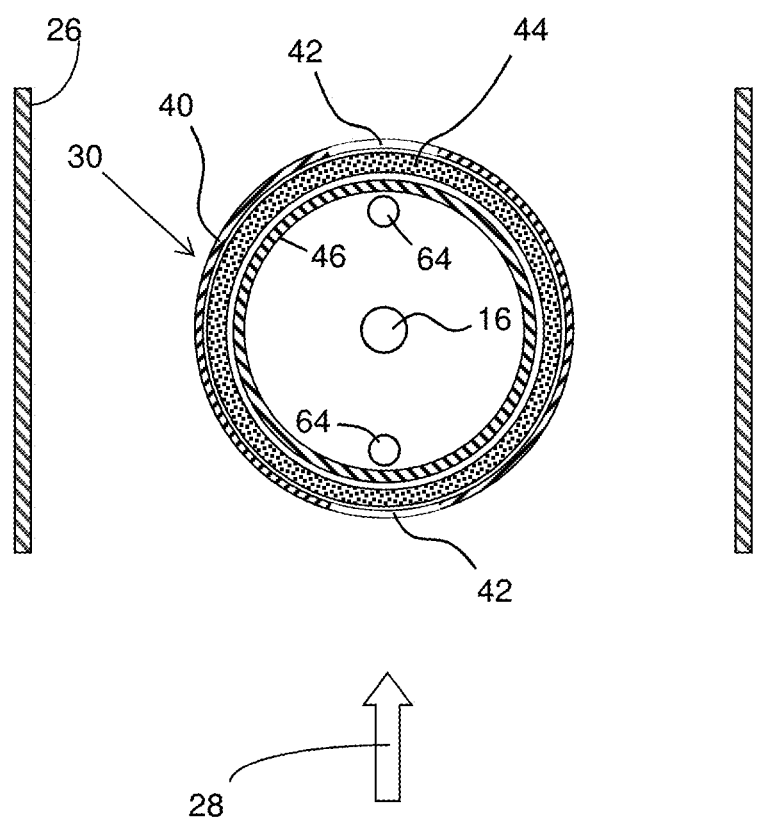
Figure 4:
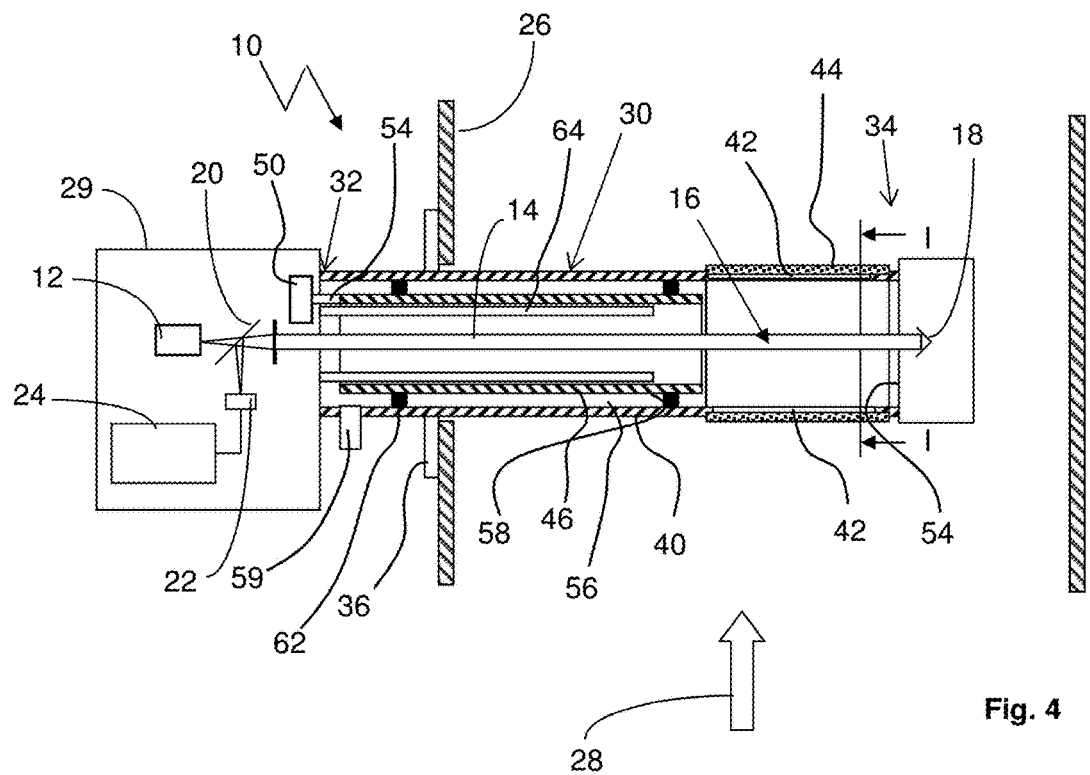

The invention will be explained in detail in the following with reference to embodiments and to the drawing. There are shown in the drawing:

FIG. 1 a schematic representation of an embodiment of the apparatus for an optical in-situ gas analysis in a gas flow;

FIG. 2 the apparatus of FIG. 1 with closed openings;

FIG. 3 the apparatus of FIGS. 1 and 2 in a section along the line I-I;

FIG. 4 a schematic representation of an embodiment; and

Figure 5:
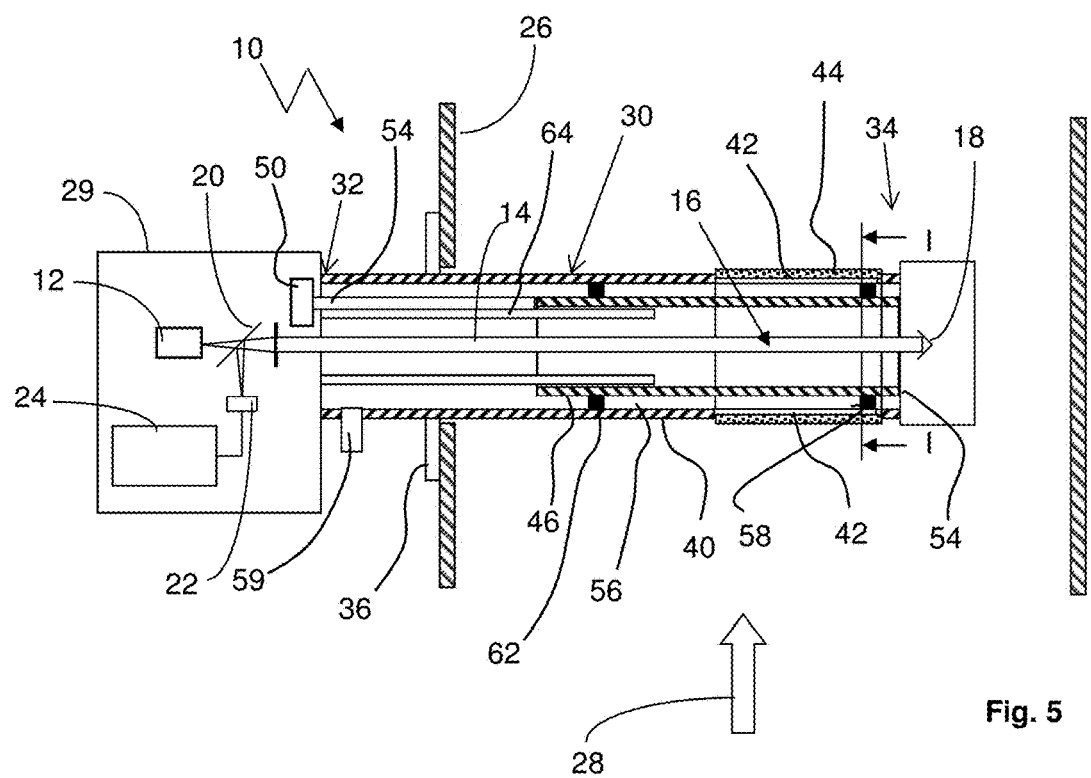

FIG. 5 the apparatus of FIG. 4 with closed openings.

An optoelectronic apparatus 10 in accordance with the invention for an optical in-situ gas analysis of a gas flow 28 that is guided in a flue gas passage has a light transmitter 12 that transmits a transmitted light beam 14 in an embodiment shown in FIG. 1. The transmitted light beam 14 defines a measurement path 16 and is received by a light receiver 22 after reflection at a retroreflector 18 and a beam splitter 20. The light receiver 22 generates received signals in dependence on the incident light that are evaluated in an evaluation device 24, for example to determine the concentration of a component of the measurement gas.

Such an optoelectronic apparatus 10 is configured as a transmissiometer in this embodiment so that the intensity of the light passing through the measurement path 16 is measured by the light receiver 22. As a rule, the light transmitter 12 is tuned to a specific wavelength which is absorbed by a gas portion to be inspected, for example hydrogen sulfide. A statement can then be made via the light received at the light receiver 22 as to how high the concentration of the gas portion of interest is in the gas flow 28 which is conducted in the flue gas passage 26.

The optoelectronic apparatus 10 comprises a housing 29 having a measuring lance 30 whose one first end 32 is connected to the housing 29 and whose other second end 34 projects into the flue gas passage 26 and thus into the gas 28 to be measured. The housing 29 and the measuring lance 30 are fixed to a wall of the flue gas passage via a fastening flange 36.

The optoelectronic units such as the light transmitter 12, the light receiver 22, and the evaluation device 24 are arranged in the housing 29 and the light is guided through the measurement path 16 in the measuring lance 30. The retroreflector 18 is held at the second end 34 of the measuring lance 30.

The measuring lance 30 has an outer pipe 40 that extends over the total length of the measuring lance 30 and that is fixed to the housing 29 at its one end and holds the retroreflector 18 at its other end. The outer pipe 40 has openings 42 in the region of the outer pipe 40 that projects into the flue gas passage 26 so that portions of the gas flow 28 can move into the measurement path 16.

The gas flow 28 that is guided in the flue gas passage 26 and that is only indicated by an arrow 28 can be loaded with particulates, for example dust, smoke or other aerosols, with the particulates interfering with the actual optical measurement on the measurement path 16. To keep the particulates away from the measurement path 16, a gas-permeable filter 44, preferably composed of porous material, is at least provided in the region of the openings 42. The filter 44 is tubular and the measurement path 16 is located in its interior.

The filter 44 is located in the interior of the outer pipe 40 in the embodiment of FIGS. 1 and 2.

The measuring lance 30 furthermore has an inner pipe 46 arranged coaxial with respect to the outer pipe 40. The inner pipe 46 is configured as displaceable with respect to the outer pipe 40 in the longitudinal pipe direction. The displacement is effected by an electric drive 50 that engages at the inner pipe 46 via a suitable mechanism 52 and that can displace it to and fro between two end positions in the longitudinal pipe direction.

The one of the end positions at which the regular measurement can be carried out (working operation) and at which measurement gas 28 can move into the measurement path 16 is shown in FIG. 1.

In the other end position, which is shown in FIG. 2, the inner pipe 46 abuts an abutment 54. The measurement gas 28 can then only move into an annular gap 56 between the inner pipe 46 and the outer pipe 40. This annular gap 56 is sealed by a piston ring 58 with respect to the housing 29. The measurement gas 28 can thus not move into the interior of the inner pipe 46 and thus not into the measurement path 16.

In this end position, the measurement path 16 can be kept free of measurement gas and a test mode of operation can take place. A test gas connector 59 is provided for this purpose. In order also actually to displace and keep away the still present measurement gas from the measurement path 16, so much test gas is let in that the pressure in the measurement path 16 is slightly higher than in the flue gas passage 26. At the same time, a defined leak is e.g. provided at the abutment 54 so that measurement gas is "flushed" out of the measurement path 16. In this sense, the openings 42 have thus been closed by displacing the inner pipe 46 into the second end position.

Guide elements are preferably provided for displacing the inner pipe 46 with respect to the outer pipe 40. They can be formed by the first piston ring 58 and by a second piston ring 62 spaced apart in the longitudinal pipe direction.

In order not to strain the seals by the piston rings 58 and 62, the guide elements can also be formed by guide bars 64 that are, for example, arranged at the housing 29 and hold the inner pipe 46 and guide it during displacement.

A material combination in which the piston rings 58 and 62 comprise bronze or brass and the outer pipe 40 comprises steel is advantageous for a good sealing and a good sliding capability.

The gas-permeable filter 44 is attached to the outside of the outer pipe in the embodiment in accordance with FIGS. 4 and 5. The piston rings 58 and 62 can thereby also slide at the outer pipe inner wall in the filter region. The spacing of the piston rings is thus additionally better distributed over the inner pipe and a canting is avoided.

The invention claimed is:

1. An apparatus for an optical in-situ gas analysis, comprising:
   a housing;
   a measuring lance whose one first end is connected to the housing and whose other second end projects into the gas to be measured;
   a light transmitter that is arranged in the housing and whose light is conducted into the measuring lance and is reflected onto a light receiver by a reflector arranged at the second end, and with the light being conducted along an optical path, with the optical path defining an optical measurement path within the measuring lance;
   a gas-permeable filter that is held in the measuring lance and in whose interior the measurement path is located; and
   an evaluation device for evaluating received light signals of the light receiver,
   wherein the measuring lance has coaxially arranged inner and outer pipes and the outer pipe has openings for the gas to be measured,
   wherein the inner pipe and the outer pipe are displaceable with respect to one another in the longitudinal pipe direction to close the openings in a test mode of operation, and
   wherein a seal seals an annular gap between the inner pipe and the outer pipe, the seal comprising a pair of longitudinally spaced apart piston rings.

2. The apparatus in accordance with claim 1, wherein the at least one piston ring comprises bronze or brass and the outer pipe comprises steel.

3. The apparatus in accordance with claim 1, wherein the inner pipe is guided by guide elements and can be displaced by an electric motor.

4. The apparatus in accordance with claim 1, wherein the inner pipe is displaceable by means of magnets fixed to the inner pipe and by means of electrically controllable magnets arranged at the guide elements.

5. The apparatus in accordance with claim 1, further comprising a test gas connector via which the measurement path can be filled with a test gas.

* * * * *